(12) United States Patent
Van Der Ende

(10) Patent No.: US 6,263,041 B1
(45) Date of Patent: Jul. 17, 2001

(54) TOMOGRAPHY DEVICE AND METHOD OF FORMING A TOMOGRAPHIC IMAGE BY MEANS OF SUCH A DEVICE

(75) Inventor: Adrianus Van Der Ende, Eindhoven (NL)

(73) Assignee: U.S. Philips Corporation, New York, NY (US)

(*) Notice: Subject to any disclaimer, the term of this patent is extended or adjusted under 35 U.S.C. 154(b) by 0 days.

(21) Appl. No.: 09/425,655

(22) Filed: Oct. 22, 1999

(30) Foreign Application Priority Data

Oct. 23, 1998 (EP) .................................................. 98203555

(51) Int. Cl.⁷ ........................................................ A61B 6/02
(52) U.S. Cl. .............................. 378/21; 378/24; 378/197; 378/205
(58) Field of Search ..................................... 378/21, 23, 24, 378/25, 26, 27, 195, 196, 197, 205

(56) References Cited

U.S. PATENT DOCUMENTS

| 2,953,683 | * | 9/1960 | Guntert | 378/21 |
|---|---|---|---|---|
| 3,746,872 | * | 7/1973 | Ashe et al. | 378/21 |
| 4,455,668 | * | 6/1984 | Warden | 378/21 |
| 5,086,448 | | 2/1992 | Muthmann | 378/187 |
| 5,095,501 | | 3/1992 | Kobayashi | 378/196 |
| 5,594,768 | * | 1/1997 | Fujii et al. | 378/21 |

FOREIGN PATENT DOCUMENTS

| 2440146 | * | 3/1976 | (DE) | 378/26 |
|---|---|---|---|---|
| WO9824368 | | 6/1998 | (WO) | A61B/6/00 |

* cited by examiner

Primary Examiner—David P. Porta
Assistant Examiner—Drew A. Dunn
(74) Attorney, Agent, or Firm—John F. Vodopia

(57) ABSTRACT

A tomography device, which includes a frame, a table for supporting a patient to be examined, an X-ray source which is pivotable about a pivot shaft in order to direct the X-rays towards the table during operation, and a receiving plate which is displaceable relative to the frame in order to pick up X-rays emitted by the X-ray source during operation. The pivot shaft is journalled in a slide which is displaceable relative to the frame by means of a guide system. The slide also accommodates the receiving plate. Because the receiving plate is part of image intensifier, the image intensifier is connected to the slide, and the slide is displaceable relative to frame, radial movement of plate occurs in a plane which is parallel to the plane of frame.

4 Claims, 5 Drawing Sheets

TOMOGRAPHY DEVICE AND METHOD OF FORMING A TOMOGRAPHIC IMAGE BY MEANS OF SUCH A DEVICE

BACKGROUND OF THE INVENTION

1. Field of the Invention

The invention relates to a tomography device which includes a frame, a table for supporting a patient to be examined, an X-ray source which is pivotable about a pivot shaft in order to direct the X-rays towards the table during operation, and a receiving plate which is displaceable relative to the frame in order to receive the X-rays emitted by the X-ray source during operation. The invention also relates to a method which is suitable for forming a tomographic image by means of such a tomography device.

2. Description of Related Art

In a device and a method of this kind which are known from international patent application WO 88/08277, the X-ray source is pivotable about a pivot shaft which is connected to the frame. A housing accommodating the receiving plate is connected to the pivot shaft. The receiving plate is displaceable relative to the housing via a guide system. The patient table is arranged on the housing. The patient table can be displaced relative to the housing by means of a second guide system.

The patient to be examined is arranged on the patient table in order to form a tomographic image. Subsequently, the patient table is displaced relative to the housing, by way of the second guide system, until the part of the patient to be examined is situated over the receiving plate. During the formation of the tomographic image, the X-ray source is pivoted about the pivot shaft and at the same time the receiving plate is displaced relative to the patient by means of the first guide system. A tomographic image of a desired plane within the patient is formed in dependence on the relative speeds and displacements of the X-ray source and the receiving plate.

It is a drawback of the known device that it requires two guide systems; this makes the device comparatively complex.

Citation of a reference herein, or throughout this specification, is not to be construed as an admission that such reference is prior art to the Applicant's invention of the invention subsequently claimed.

SUMMARY OF THE INVENTION

It is an object of the invention to provide a tomography device having a simpler construction.

This object is achieved for the tomography device according to the invention in that the pivot shaft is journalled in a slide which is displaceable relative to the frame by way of a guide system, the slide also accommodating the receiving plate.

Via the slide which is slidable on the guide system, the X-ray source and the receiving plate can be displaced together relative to the patient table, so that the X-ray source and the receiving plate can be positioned near the part of the patient to be examined. Moreover, during the formation of the tomographic image the receiving plate is displaced relative to the patient by means of the slide. Thus, only a single guide system is required. This allows for a comparatively compact construction of the tomography device.

An embodiment of the tomography device according to the invention is characterized in that the center line of the pivot shaft, extending parallel to the receiving plate, also extends through the receiving plate.

Because the center line of the pivot shaft is situated in the same plane as the receiving plate, it is comparatively easy to determine which pivoting motions must be performed by the X-ray source and which displacements must be performed by the slide in order to obtain a tomographic image of a desired plane within the patient.

A further embodiment of the tomography device according to the invention is characterized in that the device includes a controller for controlling the pivoting of the X-ray source and the displacement of the slide during operation.

The controller controls the pivoting motions of the X-ray source and the displacements of the slide in such a manner that a tomographic image can be formed of a desired plane within the patient.

BRIEF DESCRIPTION OF THE DRAWING

The invention will be described in detail hereinafter with reference to the drawings; therein.

Corresponding components are denoted by the same reference numerals in the Figures.

DETAILED DESCRIPTION OF THE PREFERRED EMBODIMENT

Figure 1:
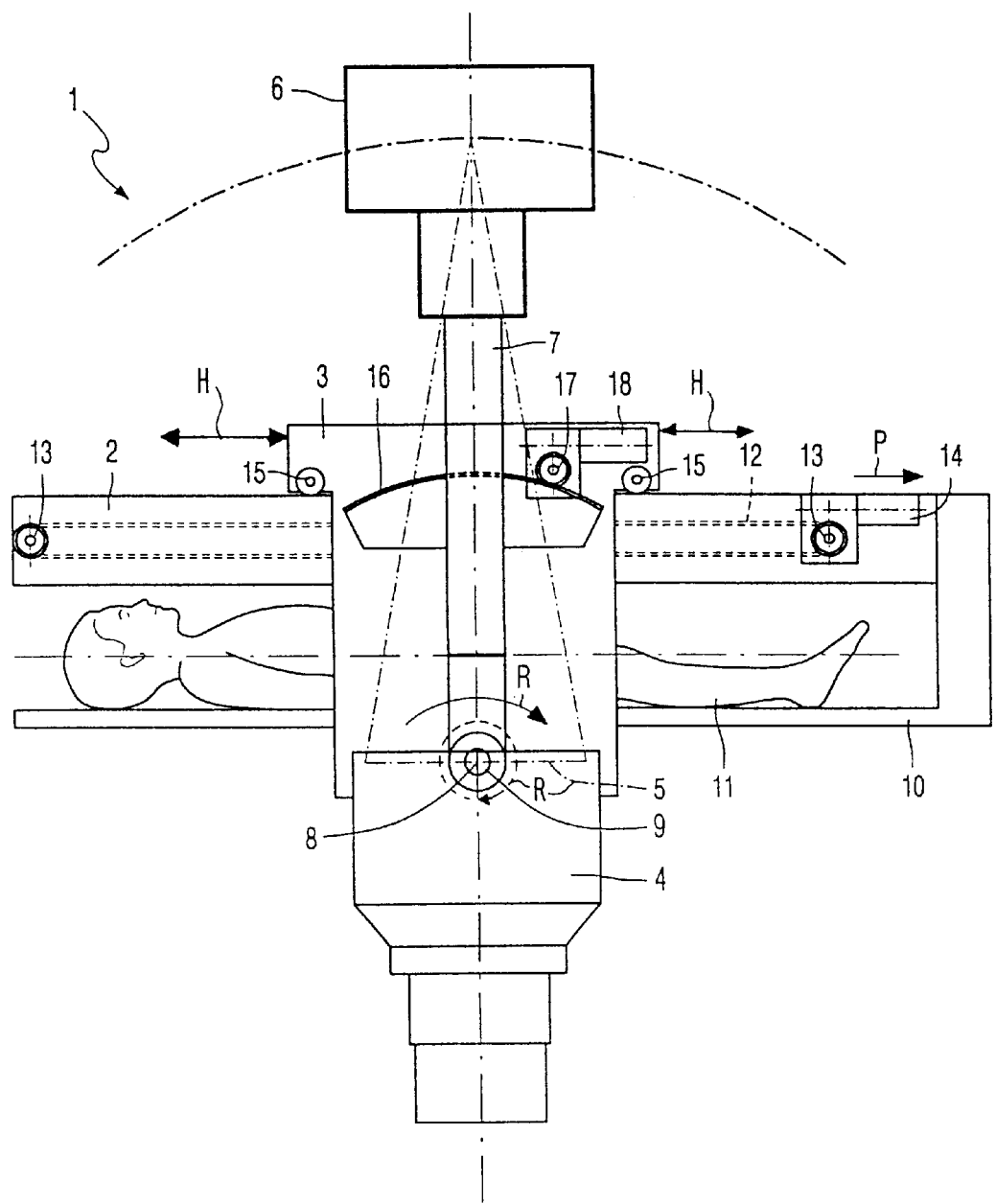
FIG. 1 is a side elevation of a first embodiment of a tomography device according to the invention.

FIG. 1 shows a tomography device 1 according to the invention which includes a frame 2, a slide 3 which is displaceable relative to the frame 2, a cassette or image intensifier 4 which is connected to the slide 3 and accommodates a receiving plate 5, and an X-ray source 6 which is connected to the slide 3, by way of an arm 7, so as to be pivotable about a pivot shaft 8. The center line 9 of the pivot shaft 8 extends parallel to the receiving plate 5 and through the receiving plate 5. The tomography device 1 also includes a patient table 10 for accommodating a patient 11.

The frame 2 is provided with an endless chain 12 which is guided on two sprockets 13. One sprocket 13 can be rotated by means of a motor 14. The chain 12 is connected to the slide 3. The slide 3 is provided with casters 15 which bear on the frame 2. When the sprocket 13 is driven by means of the motor 14, the chain 12, and hence the slide 13 connected thereto, is displaced in the direction indicated by the arrow P or in the opposite direction. More particularly, slide 3 moves in either direction H relative the surface of frame 2 when sprocket 13 is driven by motor 14. The slide 3 is also provided with a journal for the pivot shaft 8. The arm 7, connected to the pivot shaft 8, is provided with an arc-shaped rack 16. The rack 16 has a radius whose center is coincident with the center line 9. As should be clear to one skilled in the art, because receiving plate 5 is part of image intensifier 4, which image intensifier is connected to slide 3, which slide is displaceable relative to frame 2, radial movement of plate 5 occurs in a plane which is parallel to the plane of frame 2. The slide 3 is also provided with a pinion 17 which engages the rack 16. The pinion 17 is rotatable by means of a motor 18. When the pinion 17 is driven by means of the motor 18, the rack 16, and hence the arm 7 and the X-ray source 6 connected thereto, is pivoted in the direction indicated by the arrow R or in the opposite direction.

Figure 5:
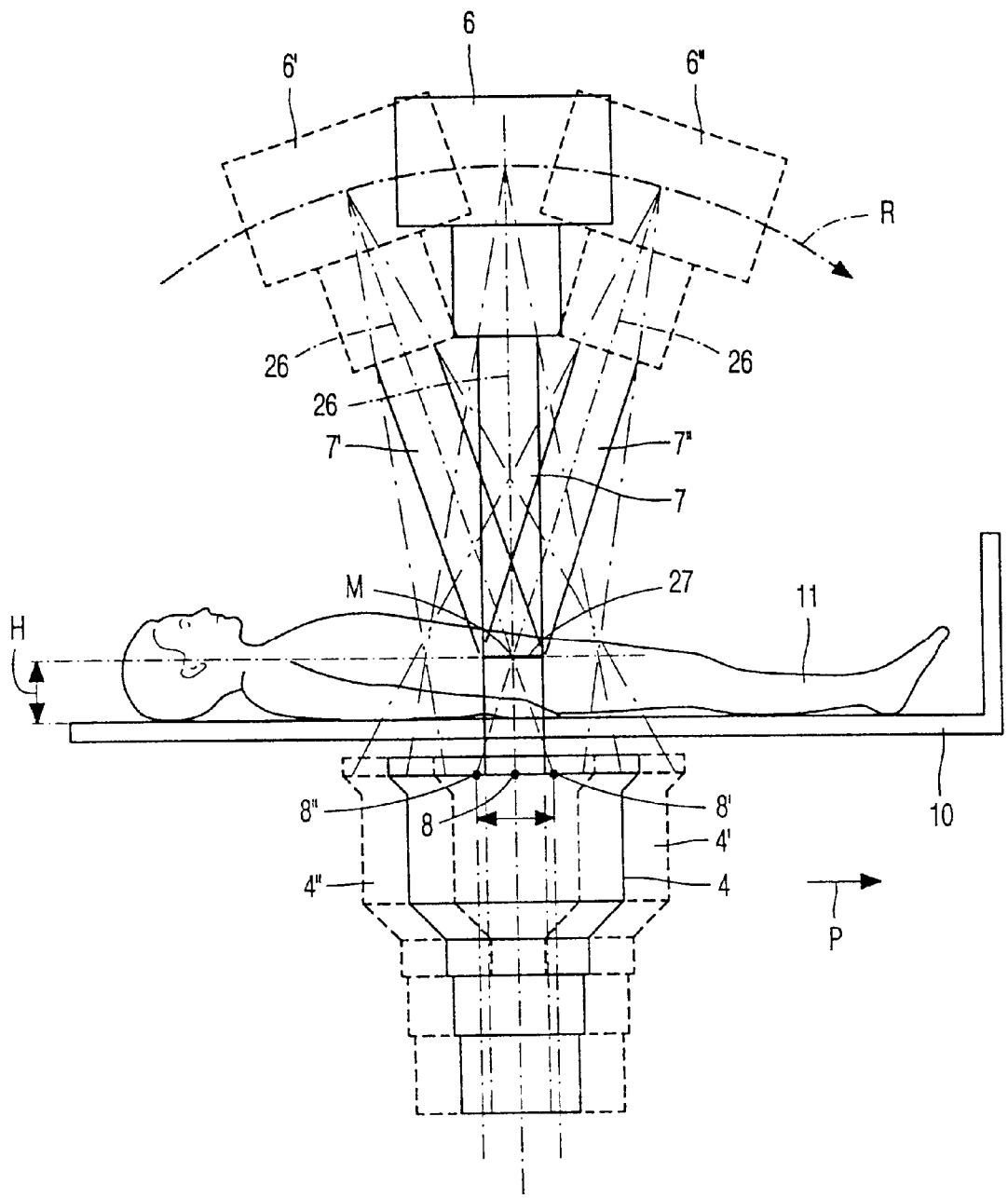
FIG. 5 is a side elevation, representing different operating positions, of a part of the tomography devices shown in the FIGS. 1 and 2.

The operation of the tomography device 1 will be described in detail with reference to FIG. 5.

Figure 2:
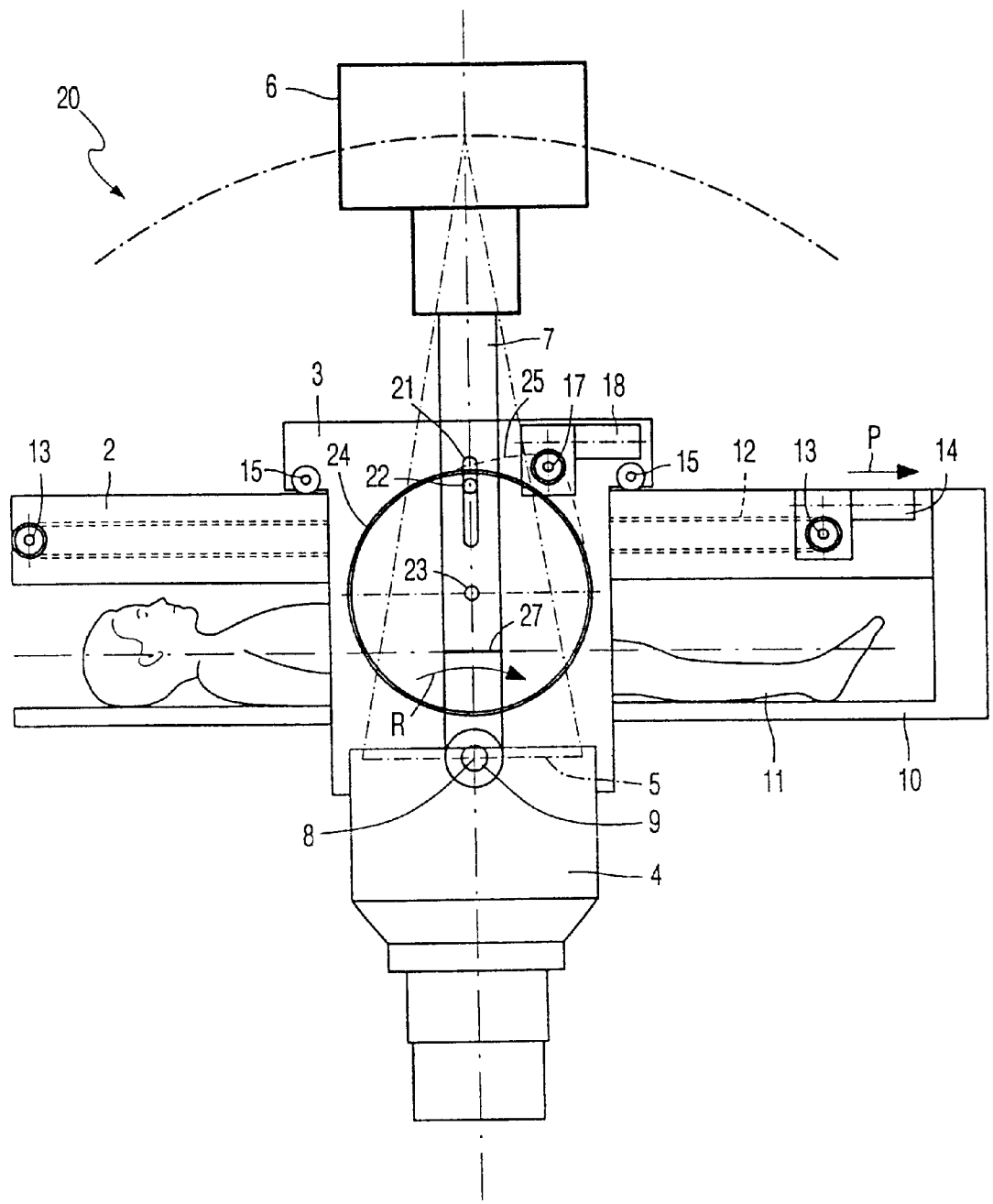
FIG. 2 is a side elevation of a second embodiment of a tomography device according to the invention.
Figure 3:
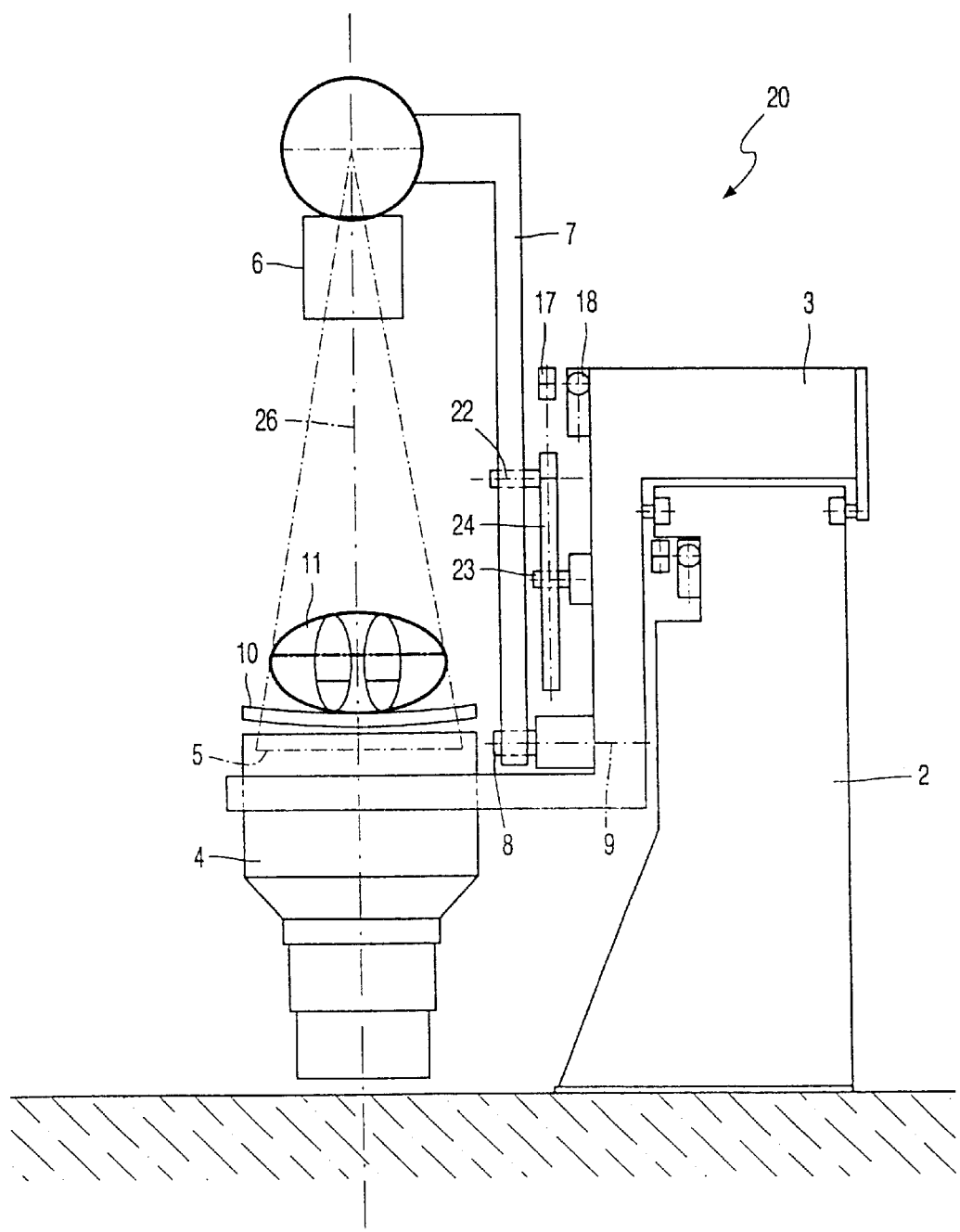
FIG. 3 is a rear view of the tomography device shown in FIG. 2.
Figure 4:
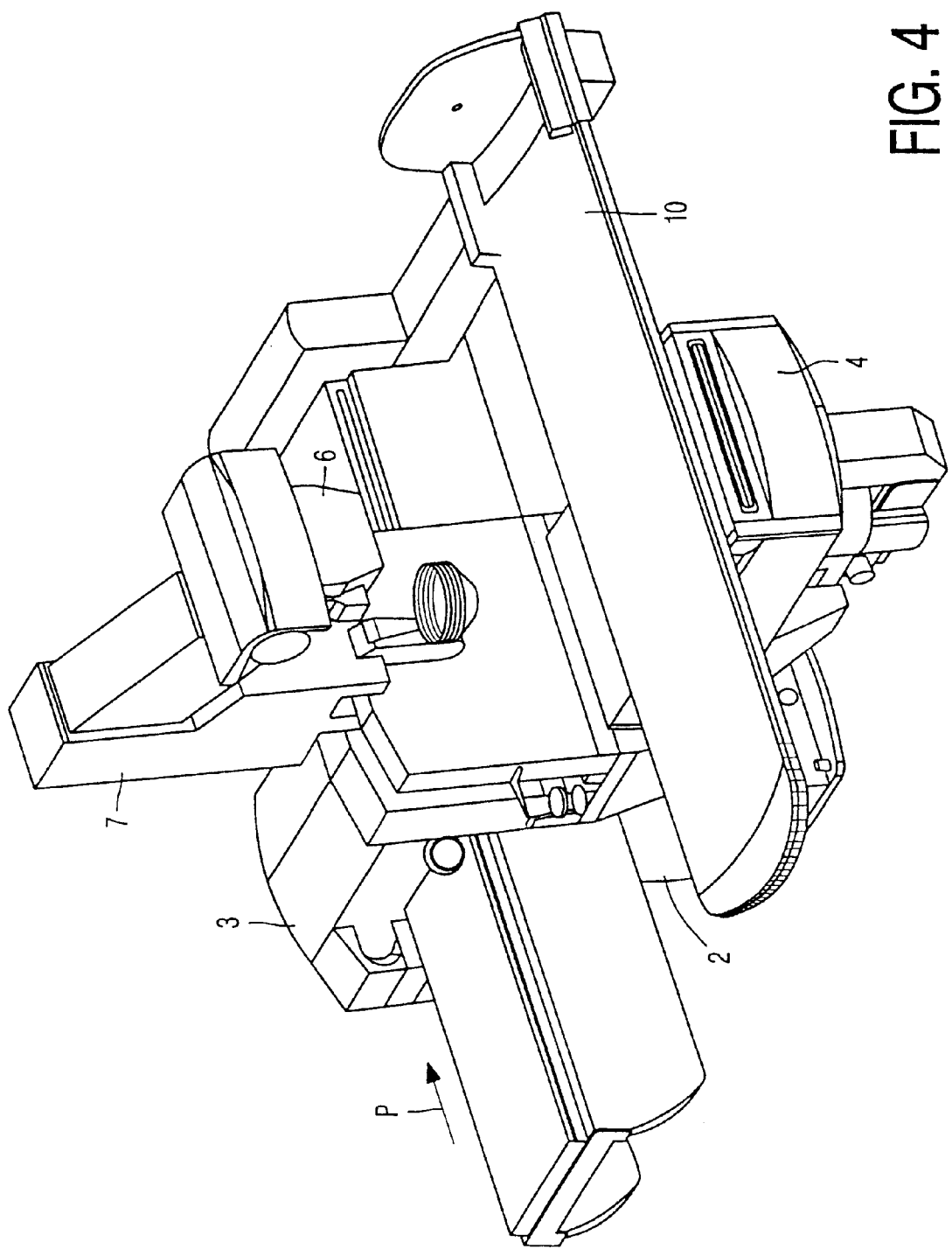
FIG. 4 is a perspective view of the tomography device shown in FIG. 2.

The FIGS. 2 to 4 show a second embodiment of a tomography device 20 according to the invention which essentially corresponds to the tomography device 1 shown in FIG. 1. In the tomography device 20 shown in the FIGS. 2 to 4, however, the X-ray source 6 is pivoted about the center line 9 in a different manner in comparison with the tomography device 1 shown in FIG. 1. The arm 7 in the tomography device 20 is provided with an elongate slot 21 which is engaged by a pin 22. The pin 22 is connected to a wheel 24 which is rotatable about a shaft 23. The shaft 23 is rotatably journalled in the slide 3. The tomography device 20 also includes a pinion 17 which is rotatable by means of a motor 18. An endless belt 25 is guided on the pinion 17 and the wheel 24. When the pinion 17 is rotated, the wheel 24 is rotated about the shaft 23 together with the pin 22. The pin 22 then pivots the arm 7 about the center line 9; the pin 22 is then displaced in the slot 21. The ends of the slot 21 define the extreme positions of the arm 7 and hence of the X-ray source 6.

The operation of the tomography device 20 and the tomography device 1 shown in FIG. 1 will now be described in detail with reference to FIG. 5. After a patient 11 has been arranged on the patient table 10, the slide 3 is displaced in the direction denoted by the arrow B1, or in the opposite direction, until the X-ray source 6, connected to the slide 3, and the receiving plate 5, arranged in the cassette or image intensifier 4, are situated near the part of the patient 11 for which a tomographic image is to be formed. Subsequently, the slide is displaced, together with the receiving plate 5 and the X-ray source 6 connected thereto, in the direction indicated by the arrow P. At the same time the X-ray source 6 is pivoted about the pivot shaft 8 in a direction which opposes that of the arrow R. The X-ray source successively occupies the positions denoted by the references 6", 6 and 6' whereas the member 4 successively occupies the positions denoted by the references 4", 4 and 4'. A central X-ray 26 emitted by the X-ray source 6 passes through a point M within the patient in any position of the X-ray source 6 and the slide 3. The point M is situated in a plane 27 for which the tomographic image is to be formed. As a result of the displacement of the X-ray source 6 and the receiving plate 5 relative to one another, a focused image is obtained only of the plane 27. In the situation shown in FIG. 5, the plane 27 is situated at a distance H from the patient table 10. A tomographic image of a plane 27 situated at any desired distance H from the patient table 10 can be obtained by controlling the speed and the displacement of the slide 3 and the rotary speed and pivoting motion of the X-ray source 6 by means of a controller.

The patient table 10 may be rigidly connected to the frame 2. It is alternatively possible to connect the patient table 10 to the frame so as to be tiltable, for example as described in the cited international patent application WO 88/08277 or in WO 97/10750.

It is alternatively possible to displace the slide 3 relative to the frame 2 by means of a different drive, for example a spindle or a toothed belt.

It is also possible for the receiving plate to form part of an X-ray image intensifier, a semiconductor X-ray detector or another X-ray detector.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A X-ray tomography device comprising:

a frame, a table for supporting a patient to be examined, an X-ray source which is pivotable about a pivot shaft in order to direct the X-rays towards the table during operation, and a receiving plate which is displaceable relative to the frame in order to receive the X-rays emitted by the X-ray source during operation, wherein the pivot shaft is journalled in a slide which is displaceable relative to the frame by way of a guide system, the slide also accommodating the receiving plate.

2. A tomography device as claimed in claim 1 wherein the center line of the pivot shaft, extending parallel to the receiving plate, also extends through the receiving plate.

3. A tomography device as claimed in claim 1 further comprising a controller for controlling the pivoting of the X-ray source and the displacement of the slide during operation.

4. A method suitable for forming a tomographic image comprising:

arranging a patient in an X-ray tomographic device as claimed in claim 1, wherein the x-ray tomographic device further comprises a controller for controlling the pivoting of the X-ray source and the displacement of the slide during operation, and using the controller to control the pivoting motion of the X-ray source and the displacement of the slide in such a manner that a tomographic image of a predetermined plane within the patient is formed.

* * * * *